United States Patent [19]

Grögler et al.

[11] 4,348,512
[45] Sep. 7, 1982

[54] POLYISOCYANATE REACTION PRODUCTS OF DIISOCYANATES AND S-TRIAZINE DERIVATIVES CONTAINING AMINO GROUPS, AND POLYMERS THEREFROM

[75] Inventors: Gerhard Grögler, Leverkusen; Holger Meyborg, Odenthal-Gloebusch, Fed. Rep. of Germany

[73] Assignee: Bayer Aktiengesellschaft, Leverkusen, Fed. Rep. of Germany

[21] Appl. No.: 206,115

[22] Filed: Nov. 12, 1980

Related U.S. Application Data

[62] Division of Ser. No. 930,611, Aug. 3, 1978, Pat. No. 4,255,570.

[30] Foreign Application Priority Data

Aug. 19, 1977 [DE] Fed. Rep. of Germany ....... 2737402

[51] Int. Cl.$^3$ ............................................. C08G 18/77
[52] U.S. Cl. ...................................... 528/73; 524/872
[58] Field of Search .......................................... 528/73

[56] References Cited

U.S. PATENT DOCUMENTS 2,838,511  6/1958  Kogon .................................. 544/221
3,210,339  10/1968  Schwarze et al. .................. 544/204

FOREIGN PATENT DOCUMENTS 955511  4/1964  United Kingdom .

*Primary Examiner*—Lewis T. Jacobs
*Attorney, Agent, or Firm*—Gene Harsh; Joseph C. Gil

[57] ABSTRACT

The invention relates to polyisocyanates corresponding to the following general formula:

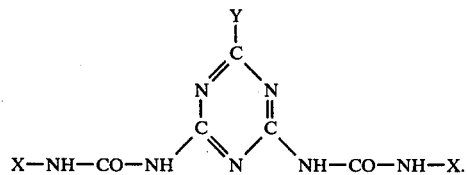

wherein
X represents a radical of the type obtained by removing the more reactive isocyanate group from an organic diisocyanate containing isocyanate groups of different reactivity; and
Y represents a chlorine, bromine, $C_1$-$C_8$ alkyl, $C_1$-$C_8$ alkoxy, $C_6$-$C_{10}$ aryl, $C_6$-$C_{10}$ aroxy radical or a radical corresponding to the general formula: —NH—CO—NH—X.

These polyisocyanates are produced by reacting polyamines corresponding to
X as shown above;
Y represents —NH—CO—NH—X.

1 Claim, No Drawings

POLYISOCYANATE REACTION PRODUCTS OF DIISOCYANATES AND S-TRIAZINE DERIVATIVES CONTAINING AMINO GROUPS, AND POLYMERS THEREFROM

This application is a division of copending application Ser. No. 930,611, filed Aug. 3, 1978, now U.S. Pat. No. 4,255,570, issued Mar. 10, 1981.

DESCRIPTION OF THE INVENTION

It has been found that melamine and other s-triazine derivatives containing amino groups may be reacted with certain diisocyanates under particular reaction conditions to form new polyisocyanates containing urea groups. The reaction surprisingly takes place without any chain-extending reaction to form corresponding polyureas.

The polyisocyanates of the present invention correspond to the following general formula:

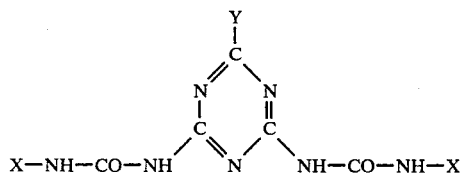

X preferably represents a radical containing isocyanate groups of the type which may be obtained by removing the isocyanate group which is more reactive in the context of the isocyanate addition reaction from an aromatic diisocyanate containing isocyanate groups of different reactivity. With particular preference, X represents a 3-isocyanato-4-methyl phenyl or a 4-(o-isocyanatobenzyl)-phenyl radical.

Y preferably represents a radical corresponding to the following general formula:

—NH—CO—NH—X wherein X preferably has the above preferred meaning and, in particular, the above particularly preferred meaning.

The compounds according to the present invention are obtained by reacting s-triazine derivatives containing amino groups and corresponding to the following general formula:

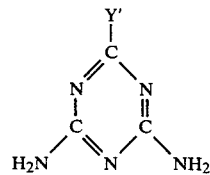

with diisocyanates corresponding to the general formula:

X—NCO wherein X is as defined above and Y' represents an NH$_2$, Cl, Br, C$_1$-C$_8$ alkyl, C$_1$-C$_8$ alkoxy, C$_6$-C$_{10}$ aryl or C$_6$-C$_{10}$ aroxy group, preferably an H$_2$N-group.

Diisocyanates corresponding to the formula, X—NCO, which are particularly suitable for use in the process according to the present invention, include an organic diisocyanates which contain isocyanate groups of different reactivity in the context of the isocyanate addition reaction and which are otherwise inert under the process conditions.

Aromatic diisocyanates corresponding to this definition are preferably used in the process according to the present invention.

The preferred aromatic diisocyanates include those having molecular weights of from 174 to 400 which, in addition to a free, i.e. sterically unhindered, aromatically bound isocyanate group, contain another aromatically bound isocyanate group which is sterically hindered by at least one substituent in the o-position. Such substituents which may lead to steric hinderance of the isocyanate group are, in particular, C$_1$-C$_8$ alkyl, C$_6$-C$_{10}$ aryl, C$_1$-C$_8$ alkoxy, C$_1$-C$_8$ thioether, C$_1$-C$_8$ alkoxy carbonyl, chlorine, bromine or cyano groups. In addition, aromatically bound isocyanate groups can be sterically hindered when the basic skeleton of the diisocyanate represents a system of several aromatic rings optionally attached through bridge members, such as alkylene, ether, thioether, sulphoxide or sulphone groups. The sterically hindered isocyanate group is situated in the ortho-position to the bridge member linking two aromatic rings.

Accordingly, suitable aromatic diisocyanates include those corresponding to general formulae (I) and (II) below:

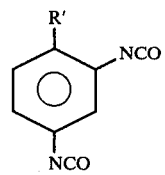

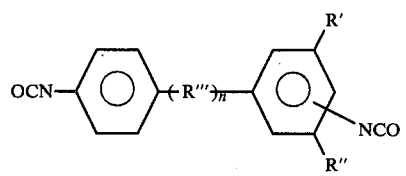

wherein

R' and R", which may be the same or different, each represents a C$_1$-C$_8$ alkyd, C$_6$-C$_{10}$ aryl, C$_1$-C$_8$ alkoxy, C$_1$-C$_8$ thioether, C$_1$-C$_8$ alkoxy carbonyl, chlorine bromine or cyano group. In addition, one of the radicals R' and R" in the compounds corresponding to general formula (II) may represent hydrogen. Also, in general formula (II), both the radicals R' and R" may represent hydrogen where the isocyanate group is situated in the ortho-position to the R''' bridge and, when n represents 0, is situated in the ortho-position to the left-hand aromatic ring;

R''' represents alkylene, ether, thioether, sulphoxide or sulphone group linking the aromatic rings; and n represents 0 or 1.

It is also possible in the process according to the present invention to use mixtures of aromatic diisocyanates containing aromatic diisocyanates with isocyanate groups of equal reactivity, such as 4,4'-diisocyanatodiphenyl methane or 2,6-diisocyanatotoluene, where the proportion of such diisocyanates containing isocyanate groups of equal reactivity does not exceed an upper limit of 50%, by weight, preferably 40% by weight, based on the mixture as a whole.

Particularly preferred diisocyanates suitable for use in the process according to the present invention include 2,4-diisocyanatotoluene, optionally in admixture with up to 50%, by weight, based on the mixture as a whole of 2,6-diisocyanatotoluene; and 2,4'-diisocyanatodiphenyl methane; optionally in admixture with up to 50%, by weight, based on the mixture as a whole, of 4,4'-diisocyanatodiphenyl methane. Other suitable diisocyanates include 2,4'-diisocyanatodiphenyl propane; 2,4'-diisocyanatodiphenyl sulphide; 2,4'-diisocyanatodiphenyl ether; 2,4'-diisocyanatodiphenyl sulphone; 2,4'-diisocyanatodiphenyl sulphodioxide; 3-methyl-4,4'-diisocyanatodiphenyl methane; 3-ethyl-4,4'-diisocyanatodiphenyl methane; 3-isopropyl-4,4'-diisocyanatodiphenyl methane; 3,5-dimethyl-4,4'-diisocyanatodiphenyl methane; 3,5-diethyl-4,4'-diisocyanatodiphenyl methane or 3,5-diisopropyl-4,4'-diisocyanatodiphenyl methane; 3-carboxymethyl-4,4'-diisocyanatodiphenyl methane; and 3-carboxyethyl-4,4'-diisocyanatodiphenyl methane.

s-triazine derivatives containing amino groups of the type mentioned above which are suitable for use in the process according to the present invention include melamine, 6-chloro-2,4-diamino-s-triazine, benzoguanamine, acetoguanamine or caprinoguanamine. Melamine is particularly preferred.

In the practical application of the process according to the present invention, the reactants are used in such quantitative ratios that the reaction mixture contains at least two isocyanate groups of the diisocyanate for every 1mino group of the s-triazine derivative. This quantitative ratio only applies to the diisocyanate containing NCO-groups of different reactivity. In general, the s-triazine derivative is stirred into an excess of the diisocyanate. The solution or dispersion formed is subsequently heated to from 60° to 180° C., preferably from 100° to 160° C., optionally in the presence of known urethanization catalysts, such as zinc acetylacetonate. The reaction continues until the isocyanate content of the reaction mixture corresponds to the theoretical content. The product of the present invention is precipitated, being insoluble in the excess diisocyanate.

After cooling of the reaction mixture to room temperature, the process products according to the present invention may be obtained in pure form by filtration and washing, for example with an inert solvent, such as acetone, chloroform or petroleum ether. The described procedure is certainly preferred because the use of an $NCO:NH_2$ equivalent ratio of $\geqq 2:1$, for example in the presence of inert solvents, yields highly cross-linked reaction products rather than the process products according to the present invention. The use of non-polar diluents which do not dissolve the process products, such as mineral spirits or aromatic hydrocarbons, although possible, is generally not necessary. In general, the excess of the diisocyanate component is selected in such a way that, for every $H_2N$-equivalent of the s-triazine polyamine the reaction mixture contains from 3 to 10, preferably from 5 to 8 NCO-equivalents, based on all the diisocyanates of the diisocyanate component.

The new compounds according to the present invention are substantially insoluble to completely insoluble in almost all the conventional organic solvents, except for highly polar solvents, such as dimethyl formamide or dimethyl sulphoxide. The new compounds have high melting points and decompose during melting. They are suitable for use as the isocyanate component in making polyurethane powder lacquers. In particular, they may also be used as active fillers in the production of polyurethane plastics by the known isocyanate polyaddition process. In this preferred use, the compounds according to the present invention are preferably dispersed in the isocyanate component used for producing the polyurethane plastic. Such dispersions in organic polyisocyanates are then processed in known manner with polyhydroxypolyethers and/or polyhydroxy polyesters, optionally in combination with known chain-extenders, to form polyurethane plastics, particularly polyurethane elastomers. Such elastomers have improved thermal stability under load, improved tear propagation resistance, improved elongation at break and improved tensile strength.

Where it is intended to use the compounds of the present invention for the production of improved polyurethane plastics of this type, there is often no need to remove the excess diisocyanate used during the production of the process products. The excess diisocyanate can directly serve as the starting component in the polyurethane reaction. In one preferred embodiment, the dispersions referred to above are reacted with the polyether polyols or polyester polyols known in polyurethane chemistry to form prepolymers containing NCO-groups in such quantitative ratios that the NCO-prepolymers formed contain both isocyanate groups emanating from unmodified diisocyanates and also the isocyanate groups of the compounds according to the present invention. These NCO-prepolymers are then reacted with chain-extenders, for example a diamine of the type exemplified in Example 10, to form a high molecular weight polyurethane polyurea. The quantity in which the chain-extender is used is either selected in such a way that approximately one isocyanate-reactive group of the chain-extender is available for all the isocyanate groups of the prepolymer including the isocyanate groups of the dispersed compounds according to the present invention, or in such a way that isocyanate-reactive groups of the chain-extender are only available for the isocyanate groups of the prepolymer which do not emanate from the compounds according to the present invention. Subsequent chemical incorporation of the initially dispersed compounds according to the present invention are obtained by tempering the reaction products at from 100° to 150° C. (cf. Example 10). It is advisable, particularly in the first-mentioned case of the use in substantially equivalent quantities of the chain-extender, based on the total quantity of isocyanate groups present, for the known polyurethane catalysts, such as dibutyl tin dilaurate, tin dioctoate, diazabicyclooctane and/or dimethyl tetrahydropyrimidine, to be present.

EXAMPLES

Example 1

A mixture of 1000 g (5.75 mols) of tolylene diisocyanate(2,4- and 2,6-isomers in a ratio of 80:20) and 72.5 g (0.575 mol) of melamine are heated with vigorous stirring for 3 hours at from 120° to 130° C. After the reaction mixture has cooled, the reaction product is filtered under suction and washed with acetone until free from isocyanate. Vacuum drying leaves 373 g of a colorless product which is extremely difficult to dissolve in organic solvents. Yield, based on an addition product of melamine and tolylene diisocyanate in a molar ratio of 1:3, 98%, m.p.=350–380 (D).

Analysis: (MW 648) $C_{30}H_{24}N_{12}O_6$

|  | C | H | N |
|---|---|---|---|
| calculated: | 55.4 | 3.7 | 26.0 |
| observed: | 55.6 | 3.7 | 26.3 |

The diisocyanate reacts only slowly with aliphatic amines, such as di-n-butylamine, at room temperature. Accordingly, the NCO-value at room temperature may only be determined after a prolonged reaction time:

| Titration time (mins) | NCO (%) |
|---|---|
| 15 | 5.5 |
| 30 | 10.8 |
| 60 | 14.7 |
| 120 | 19.0 |

If, by contrast, titration is carried out at from 50° to 70° C., an NCO-value of 19.3% (calculated 19.5%) is obtained after only from 3 to 5 minutes.

Example 2 (Comparison)

A mixture of 63 g (0.5 mol) of melamine and 3.3 g (1.8 mol) of the tolylene diisocyanate of Example 1 in 1 liter of nitrobenzene is heated to 140° C. After 45 minutes, the reaction mixture may no longer be stirred. It is diluted with acetone and filtered under suction. The dried deposit has an NCO-value of 2.5% (calculated 19.5%).

Example 3 (Comparison)

31.5 g (0.25 mol) of melamine and 480 g (3 mols) of 1,3-phenylene diisocyanate are heated with vigorous stirring for 7 hours to from 100° to 140° C. The reaction mixture is then diluted with chloroform and filtered under suction. The vacuum-dried deposit has an NCO-value of 10.9% (calculated 20.8%).

Example 4

31.5 g (0.25 mol) of melamine and 500 g (2 mols) of a diphenyl methane diisocyanate containing approximately 40% of 4,4'-isomers and 60% of 2,4'-isomers are heated with vigorous stirring for 4 hours to 100° C. The reaction mixture is then diluted with chloroform/petroleum ether and filtered under suction. The deposit is vacuum dried.

Yield 200 g (91%). Melting point 252°–260° C. (decomposition).

Analysis (MW 876) $C_{48}H_{36}N_{12}O_6$

|  | C | H | N |
|---|---|---|---|
| calculated: | 65.8 | 4.12 | 19.2 |
| observed: | 65.4 | 3.90 | 18.0 |
| NCO-value 13.9% (theoretical 14.4%). | | | |

Example 5 (Comparison)

A mixture of 12.6 g (0.1 mol) of melamine and 250 g (1 mol) of molten 4,4'-diphenylmethanediisocyanate is heated to 120° C. After 30 minutes, the reaction mixture is solid.

Example 6

7.6 g (0.06 mol) of melamine and 252 g (1 mol) of 2,4'-diisocyanatodiphenyl ether are heated for 4 hours to 100° C. The reaction mixture is then diluted with methylene chloride/petroleum ether and filtered under suction. The deposit is vacuum dried.

Yield 48 g (91%). Melting point 265°–268° C.

Analysis: (MW 882) $C_{45}H_{30}N_{12}O_9$

|  | C | H | N |
|---|---|---|---|
| calculated: | 61.2 | 3.4 | 19.0 |
| observed: | 59.8 | 3.1 | 18.5 |
| NCO-value 13.1% (theoretical 14.3%). | | | |

Example 7

0.567 kg (4.5 mols) of melamine are added with stirring at room temperature to 7.1 kg (40.8 mols) of 2,4-tolylene diisocyanate. The reaction mixture is heated to from 125° to 130° C. After 2 hours, it is cooled to from 80° to 85° C. The excess 2,4-tolylene diisocyanate containing the melamine triisocyanate in the form of a finely divided suspension is then pre-polymerized with 27.31 kg (13.7 mols) of a difunctional polypropylene glycol (OH-number 56). After from 4 to 5 hours at from 80° to 85° C., the prepolymer has an NCO-value of from 3.2 to 3.4%. If the NCO-determination is carried out with heating or in dimethyl sulphoxide solution, an NCO-value of from 4.4 to 4.6% is determined because, in that case, the NCO-content of the melamine-diisocyanate adduct is also included.

The prepolymer has a solids content of 8.4% and a viscosity of 4500 cP (25° C.).

Example 8

14.4 g (0.11 mol) of melamine and 336 g (1.34 mol) of a diphenyl methane diisocyanate containing approximately 40% of 4,4'-isomers and 60% of 2,4'-isomers are heated with vigorous stirring for 4 hours to 100° C. 1000 g of a difunctional polyether diol (OH-number 28) are then added at 80° C. After 3 hours at 90° C., the prepolymer has an NCO-value of 3.6%. Its solids content amounts to 7.4%.

Example 9

27.5 g (0.24 mol) of ethylene glycol monobutyl ether in 100 ml of chlorobenzene are mixed with 50 g (0.08 mol) of the compound isolated in Example 1. The reaction mixture is heated to 130° C. After 90 minutes, it may no longer be stirred. Following the addition of 0.5 g of dibutyl tin dilaurate under otherwise the same conditions, the reaction mixture may no longer be stirred after only 20 minutes. Where 0.5 g of dimethyl tetrahydropyrimidine is added, the reaction mixture is no longer stirrable after only 40 minutes. Accordingly, the triisocyanate reacts off under the conventional conditions to form the urethane.

Example 10

100 parts by weight, of the modified NCO-prepolymer produced in Example 7 are degassed in vacuo at from 60° to 80° C. and subsequently stirred for 30 seconds with 6 parts, by weight, of 3,5-diethyl-1-methyl-2,4-diaminobenzene. Separate halves of the reaction mixture are then cast into metal molds heated to from 110° to 130° C., respectively. The casting time is approximately 2 minutes. After from 4 to 5 minutes, the casting may be removed from the mold. After tempering at 110° C. (24 hours) and at 130° C., the mechanical properties of the elastomer are determined:

|  | Tempering temperature | |
| --- | --- | --- |
|  | 110° C. | 130° C. |
| Tensile strength (DIN 53504) | 7.5 MPa | 14.0 MPa |
| Elongation at break (DIN 53504) | 350% | 650% |
| Tear propagation resistance (DIN 53515) | 170 N | 230 N |
| Shore hardness A (DIN 53505) | 77 | 76 |
| Elasticity (DIN 53512) | 60 | 60 |

It may be seen from the increase in tensile strength, elongation at break and tear propagation resistance that the filler is only incorporated into the PU-matrix after tempering of the elastomer at 130° C., which is clearly reflected in the reinforcing effect.

What is claimed is:

1. A process for the production of polyurethane resins comprising reacting (A) polyisocyanates with (B) compounds cntaining active hydrogen atoms, (C) fillers optionally in the presence of (D) catalysts and other known additives wherein said fillers comprise polyisocyanates of the general formula

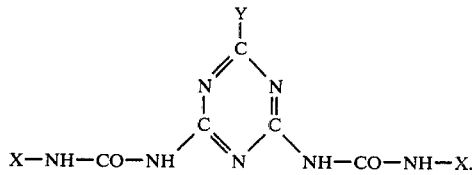

wherein

X represents a radical of the type obtained by removing the more reactive isocyanate group from an organic diisocyanate containing isocyanate groups of different reactivity; and Y represents a chlorine, bromine, $C_1$-$C_8$ alkyl, $C_1$-$C_8$ alkoxy, $C_6$-$C_{10}$ aryl, $C_6$-$C_{10}$ aroxy radical or a radical corresponding to the general formula: —NH—CO—NH—X.

* * * * *